US00PP34881P2

(12) United States Plant Patent
Bourne

(10) Patent No.: US PP34,881 P2
(45) Date of Patent: Jan. 3, 2023

(54) GRAPEVINE PLANT NAMED 'SV35-186-427'

(50) Latin Name: ***Vitis* ssp.**
Varietal Denomination: SV35-186-427

(71) Applicant: Sunview Vineyards of California, Inc., Delano, CA (US)

(72) Inventor: Timothy F Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 17/803,256

(22) Filed: Apr. 4, 2022

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 6/88; A01H 5/08
See application file for complete search history.

*Primary Examiner* — Keith O. Robinson
(74) *Attorney, Agent, or Firm* — Eric C. Cole; Baker Manock & Jensen, PC

(57) ABSTRACT

A new and distinct variety of grapevine plant named 'SV35-186-427' particularly characterized by its very sweet, crisp, red berries with flavor similar to spun sugar. Natural cluster size is medium with well-filled, loose clusters. Fruitfulness is high with shoots on spur pruned vines usually producing two flower clusters per shoot. Vine vigor is very high with canes producing 365.5 cm of growth per shoot.

3 Drawing Sheets

Scientific name of the genus and species of the plant claimed: The plant claimed relates to a new and distinct variety of *Vitis* ssp.

Variety denomination: The plant claimed shall be known as 'SV35-186-427'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis* spp. and hereinafter referred to as grapevine named 'SV35-186-427'. As used herein, 'grapevine' refers to all plant parts including, vines, canes, tendrils, leaves, fruit and roots of grapevine named 'SV35-186-427'. Grapevine named '35-186-427' is the result of an effort to produce a crisp, seedless table grape with flavor similar to spun sugar. This new cultivar originated from a cross conducted in May 2014 near McFarland, Calif. between female grapevine plant selection 'SV24-14-164' (unpatented) and male grapevine plant 'SV22-88e-124' (U.S. Plant Pat. No. 31,992). Resultant ovules from the cross were harvested 42 days after pollination and cultured on 'McCown's Woody Plant Medium'. Subsequently, the resultant embryonic plants were cultured in the same medium in the laboratory under twelve hours of light from standard fluorescent lamps at 27° C. The seedlings from this effort were transplanted to the greenhouse in November of 2014 and grown at 27° C. with 12 hours illumination under high pressure sodium vapor lamps. The seedling population was planted in the field in the spring of 2015 near Delano, Calif. The new grapevine was selected from this seedling population on Sep. 29, 2017. It was then propagated by cuttings and bench grafted to 'Freedom' (unpatented) rootstock in 2018. The present invention has been found to retain its distinctive characteristics through three successive asexual propagations.

Grapevine named 'SV35-186-427' differs from its female parent grapevine 'SV24-14-164' (unpatented) in that 'SV35-186-427' has ellipsoidal to ovate shaped, seedless berries with spun sugar flavor, whereas 'SV24-14-164' has red, spherical shaped berries with a slight muscat flavor.

Grapevine named 'SV35-186-427' differs from its male parent grapevine 'SV22-88e-124' (U.S. Plant Pat. No. 31,992) in that 'SV35-186-427' has red berries while "SV22-88e-124' (U.S. Plant Pat. No. 31,992) has golden berries also with spun sugar flavor.

Grapevine named 'SV35-186-427' is most similar to commercially available 'IFG Seven' (U.S. Plant Pat. No. 23,399) in that both cultivars have flavor similar to spun sugar. Grapevine named 'SV35-186-427' differs from the commercial cultivar 'IFG Seven' (U.S. Plant Pat. No. 23,399) in that 'SV35-186-427' has small, red berries with very crisp texture while 'IFG Seven' (U.S. Plant Pat. No. 23,399) has green, very large berries with soft texture.

Grapevine 'SV35-186-427' is similar in appearance to commercially available 'Crimson Seedless' (unpatented), both having small, red berries. Grapevine named 'SV35-186-427' differs from 'Crimson Seedless' (unpatented) in that 'SV35-186-427' has berries with spun sugar flavor while 'Crimson Seedless' (unpatented) has berries which are neutral flavored, typical of most *Vitis vinifera* table grape cultivars.

SUMMARY OF THE INVENTION

The following are the most outstanding and distinguishing characteristics of this new variety when grown under normal horticultural practices near McFarland, Calif.:

1. Fruit clusters with red berries
2. Very crisp berry texture; and
3. Small, ellipsoidal to ovate shaped berries with flavor similar to spun sugar.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The photographs were taken from the original two year old seedling vine in 2017 and from a one and a half year old vine grafted to 'Freedom' rootstock in September of 2019.

DETAILED BOTANICAL DESCRIPTION

Figure 1:
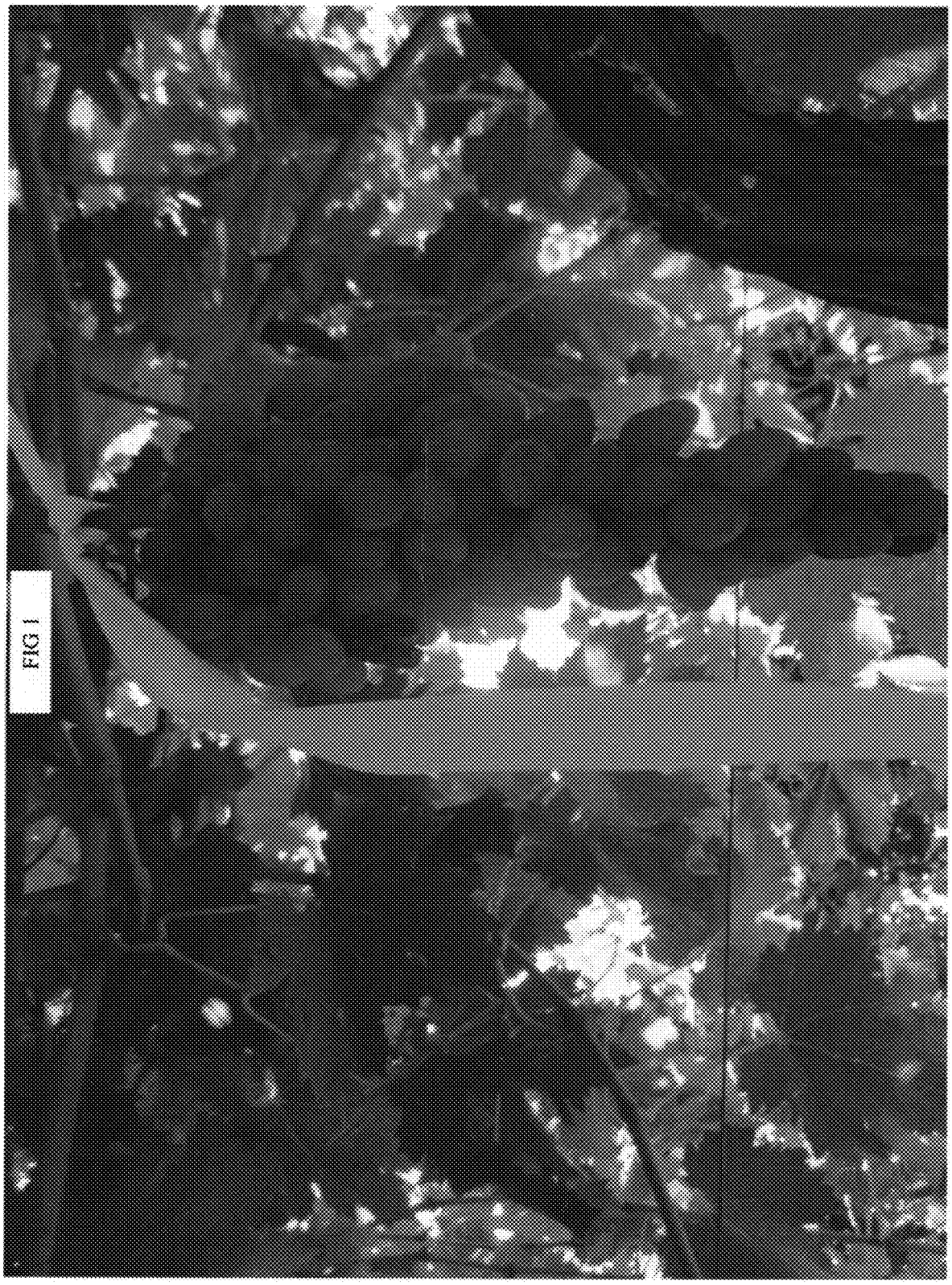
FIG. 1 Fruit cluster on the seedling vine.
Figure 2:
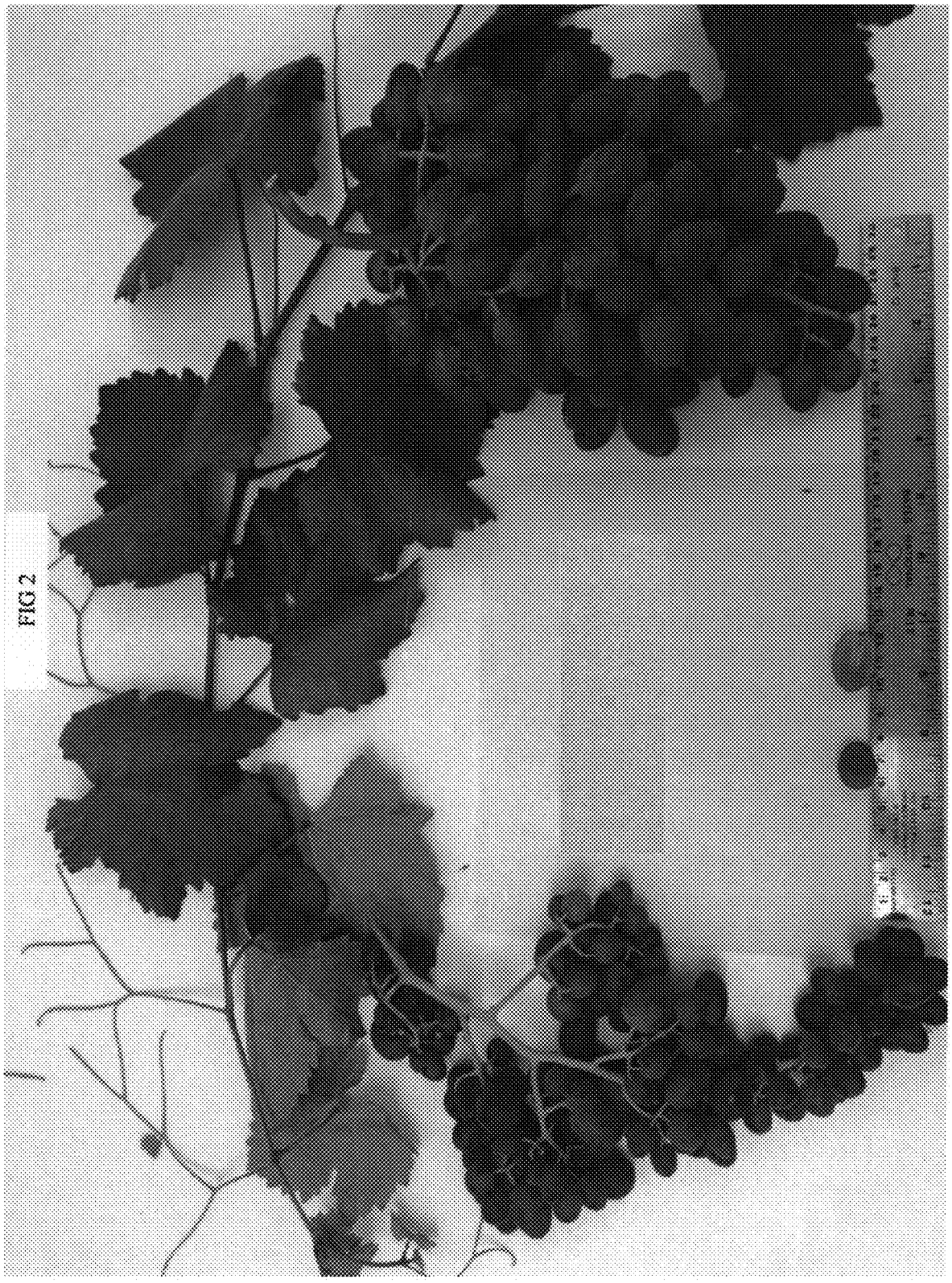
FIG. 2 Fruit cluster natural at left, from vine treated with exogenous gibberellic acid, shoots, leaves and tendrils, at right.
Figure 3:
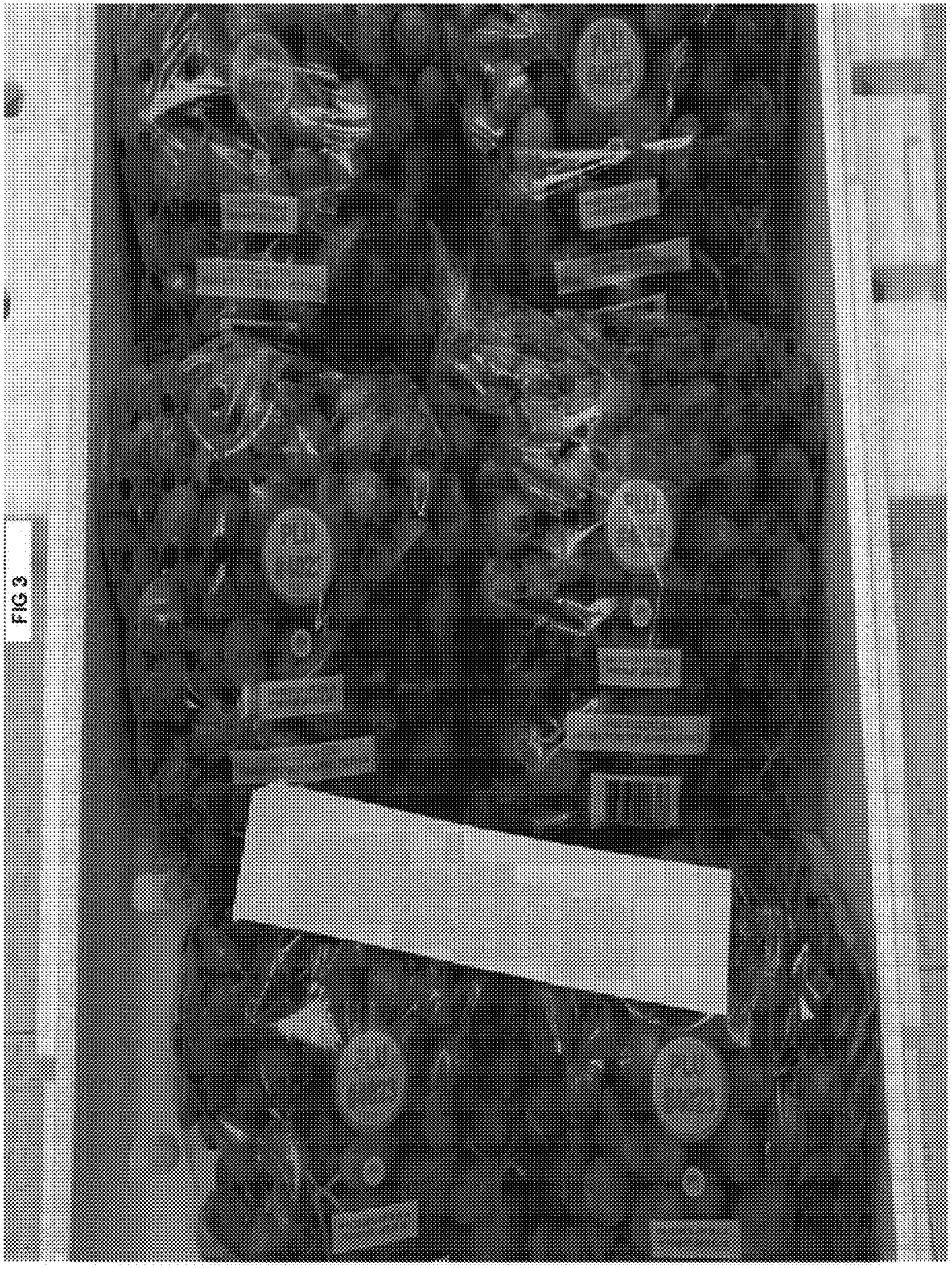
FIG. 3 Fruit clusters packed for storage testing.

The following detailed description sets forth the distinctive characteristics of grapevine named 'SV35-186-427'. Descriptions of the new invention apply to vines of 'SV35-186-427' grown on 'Freedom' (unpatented) rootstock at a density of 1,537 vines per hectare grown near McFarland, Calif. in 2019 and 2020. These vines were observed at one year and two years of age in 2019 and 2020, respectively, in the immediate year following planting and the following year of full production having been planted in 2018. These descriptions are believed to apply generally to the new variety grown under similar circumstances elsewhere. Color references are primarily to The Royal Horticultural Society's Colour Chart, The Royal Horticultural Society, London, United Kingdom (copyright 2001). Descriptors used herein conform to those set forth by the International Board for Plant Genetic Resources Institute Grape Descriptors (*Vitis* spp.) of 1983 and/or 1997 which were developed in collaboration with the Office Interantional de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

*Family*.—Vitaceae.

*Botanical name*.—*Vitis* interspecific hybrid.

*Variety name*.—'SV35-186-427'.

Plant:

*Vigor*.—High. Vines spur-pruned and shoot thinned to 32 shoots average 365.5 cm of growth per cane.

*Density of foliage*.—Heavy.

*Productivity*.—High when spur pruned, up to 50, 722 kg/hectare.

*Hardiness*.—Hardiness observed to 0° C.

*Rootstock*.—'Freedom' (unpatented).

*Bud burst*.—Medium

Trunk:

*Shape*.—Broadly elliptical.

*Straps*.—Long, split.

*Surface texture*.—Shaggy.

*Trunk circumference*.—22 cm at 1.0 m of height of 3 year old plants.

*Inner bark color*.—RHS Greyed orange group 166C.

*Outer bark color*.—RHS Grey brown group 199C.

Mature leaves:

*Average blade length*.—22.3 cm.

*Average blade width*.—20.7 cm.

*Size of blade*.—Very large.

*Shape*.—Pentagonal.

*Number of distinct lobes*.—3 or 5.

*Anthocyanin coloration of main veins on the upper side of the blade*.—Present on sun exposed leaves at base of main veins, RHS Red Purple group 60B.

*Mature leaf profile*.—Undulating.

*Blistering* (*upper surface*).—Absent.

*Leaf blade tip*.—In plane of blade.

*Margins*.—Lobed, serrated.

*Apex*.—Broadly acuminate.

*Bases*.—Sagittate.

*Thickness*.—Medium.

*Undulation of blade between main and lateral veins*.—Slight.

*Shape of teeth*.—Broadly conical, both sides convex.

*Length of teeth*.—3-15 mm, averaging 7.7 mm.

*Ratio length/width of teeth*.—3:5.

*General shape of petiole sinus*.—Wide open.

*Tooth at petiole sinus*.—Absent.

*Petiole sinus limited by veins*.—Absent.

*Depth of upper lateral sinus*.—Medium.

*Shape of upper lateral sinus*.—Closed.

*Prostrate hairs between veins* (*lower surface*).—Absent.

*Erect hairs between veins* (*lower surface*).—Absent.

*Prostrate hairs on main veins* (*lower surface*).—Absent.

*Density of erect hairs on main veins* (*lower surface*).—Sparse except at vein junctions. where erect hairs are numerous.

*Prostrate hairs on main veins* (*upper surface*).—Absent.

*Upper surface*.—Summer color: Yellow Green group 141A. Surface texture: Smooth. Surface appearance: Dull (not glossy). Goffering of blade: Absent. Pubescence: None.

*Lower surface*.—Summer color: RHS Green group 137A. Anthocyanin coloration of main veins on lower leaf surface: Restricted to bases, Red purple group 60B. Anthocyanin coloration on laterals: Absent. Glossiness: Low. Pubescence: Absence. Surface texture: Rough. Surface appearance: Dull.

*Petiole*.—Length: 10-19 cm, averaging 13.5 cm. Diameter: 4 mm. Length of petiole compared to middle vein: About 1:2. Density of prostrate hairs: Absent. Density of erect hairs: Absent. Color: In shade: RHS Yellow Green group 144B. In sun: RHS Red Purple group 60B.

Tendrils:

*Number*.—Bifurcated and trifurcated; forming at alternate nodes above node 4.

*Length*.—15.9 cm.

*Diameter*.—3 mm.

*Texture*.—Smooth.

*Summer color*.—Yellow green group 144A.

*Autumn color*.—Yellow green group 144A developing into Red purple group 60B.

Growing tips (young shoot):

*Pubescence*.—Sparse, prostrate.

*Color*.—RHS Yellow Green group 144A.

*Anthocyanins*.—Absent.

*Shape*.—Flattened.
*Apex*.—Fully open.
*Shoot attitude*.—Semi-erect.

Green summer shoots:

*Internode color upper surface*.—In sun: RHS Red purple group 60A; In shade: RHS Yellow Green group 144A.
*Internode color lower surface*.—In sun: RHS Yellow Green group 144B; In shade: RHS Yellow Green group 144B.
*Node color upper surface*.—In sun: RHS Red Purple group 60A; In shade: RHS Yellow Green group 144A.
*Node color lower surface*.—RHS Yellow Green group 144A.
*Erect hairs on internode*.—Yes.

Woody shoot:

*Canes*.—Shape: Broadly elliptic. Internode length: About 10.8 cm. Width at node: About 10.6 mm. Surface: Smooth. Main color: RHS Greyed orange group 164A. Lenticels: Inconspicuous.
*Buds*.—Shape: Pointed. Cane bud fruitfulness: Shoots from the basal two buds generally bear two flower clusters. Length: 5.2 mm. Width: 4.8 mm. Height: 5.2 mm. Color: RHS Greyed Orange group 175B.

Flowers:

*Flower sex*.—Hermaphrodite.
*Date of full bloom*.—May 10, 2021.

Fruit:

*Ripening period*.—Late September, Delano, Calif.
*Date of ripening*.—Oct. 5, 2021 at McFarland, Calif.
*Use*.—Fresh market.
*Keeping quality*.—Very good.
*Shipping quality*.—Good.
*Solids-sugar*.—High, about 21 brix at full maturity.
*Refractometer test*.—21 brix.
*Total acidity*.—0.20 g/liter.
*pH*.—4.53.
*Bunch*.—Size: Medium. Length (peduncle excluded): About 22.9 cm. Width: About 13.8 cm. Mass: Natural, without gibberellic acid treatment: 368 g. With gibberellic acid treatment: 330 g. Density: Well filled but loose. Number of berries (without gibberellic acid treatment): 161. Number of berries (with gibberellic acid treatment: 108. Form: Cylindrical.
*Peduncle*.—Length: About 6.6 cm. Lignification: 2 cm of peduncle. Main color: Fresh: RHS Green group 143A. Lignified: RHS Greyed orange group 175A.
*Berry*.—Size: Small. Uniformity of size: Uniform. Weight Natural, without gibberellic acid treatment: 3.1 g. With gibberellic acid treatment: 5.6 g. Shape: Natural, without gibberellic acid treatment: Elliptic. With gibberellic acid treatment: Elliptic to ovate. Presence of seeds: Seedless; most berries develop one or two small, soft rudimentary seeds less than 1.0 mm in length. Cross section: Circular. Dimensions: Length: Natural: 2.0 cm. With gibberellic acid treatment: 2.8 cm. Width: Natural: 1.6 cm. With gibberellic acid treatment: 2.0 cm. Skin color (without bloom): RHS Red purple group 59A. Coloration of flesh: Translucent; lack of color. Juiciness of flesh: Very juicy. Berry firmness: Very crisp. Particular flavor: Similar to spun sugar. Bloom (cuticular wax): Strong. Pedicel length: 8 mm. Berry separation from pedicel: Moderately easy.
*Skin*.—Thickness: Medium. Texture: Crisp. Reticulation: Absent. Roughness: Absent. Tenacity: Tenacious to flesh. Tendency to crack: Resistant.

Disease and insect resistance: No particular resistance or susceptibility has been observed. Normal disease control practices can be used.

Having thus described and illustrated our new variety of grapevine, we claim:

1. A new and distinct variety of grapevine plant named 'SV35-186-427', substantially as illustrated and described herein.

* * * * *